US008444838B2

(12) United States Patent
Amshey et al.

(10) Patent No.: US 8,444,838 B2
(45) Date of Patent: May 21, 2013

(54) METHODS, COMPOSITIONS, AND KITS FOR PROTEIN CRYSTALLIZATION

(75) Inventors: Joseph Amshey, Encinitas, CA (US); Thomas Diller, San Diego, CA (US); Regina Rooney, La Jolla, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1090 days.

(21) Appl. No.: 12/392,851

(22) Filed: Feb. 25, 2009

(65) Prior Publication Data

US 2009/0218547 A1 Sep. 3, 2009

Related U.S. Application Data

(63) Continuation of application No. 10/996,737, filed on Nov. 24, 2004, now abandoned.

(60) Provisional application No. 60/525,811, filed on Nov. 28, 2003.

(51) Int. Cl.
*G01N 27/447* (2006.01)
*G01N 27/453* (2006.01)

(52) U.S. Cl.
USPC .......................................... 204/548; 204/459

(58) Field of Classification Search
USPC ................................................ 204/459, 548
See application file for complete search history.

(56) References Cited

U.S. PATENT DOCUMENTS

| 4,504,641 | A | 3/1985 | Nochumson |
| 4,542,200 | A | 9/1985 | Nochumson |
| 6,468,759 | B1 | 10/2002 | Charych |
| 2001/0027745 | A1 | 10/2001 | Weigl et al. |
| 2002/0065392 | A1 | 5/2002 | Shatterjee et al. |
| 2002/0187513 | A1 | 12/2002 | Kopf-Sill et al. |
| 2003/0157482 | A1 | 8/2003 | Keesee et al. |
| 2005/0103629 | A1 | 5/2005 | Diller et al. |
| 2006/0228346 | A1 | 10/2006 | Klippel et al. |

FOREIGN PATENT DOCUMENTS

| WO | WO01/01139 | 1/2001 |
| WO | WO02/066162 | 8/2002 |
| WO | WO02/092200 | 11/2002 |
| WO | WO2005/054548 | 6/2005 |

OTHER PUBLICATIONS

Alexander McPherson "Two approaches to the rapid screening of crystallization conditions," Journal of Crystal Growth 122 (1992) 161-167.*

Righetti et al. "Review—Protein purification in multicomponent electrolyzers with isoelectric membranes," Journal of Chromatography B, 699 (1997) 105-115.*

Bott et al. "Improving the Quality of Protein Crystals through Purification by Isoelectric Focusing" The Journal of Biological Chemistry vol. 257, No. 17, issue of Sep. 10, 1982 pp. 9883-9886.*

Ali-Khan et al., "Overview of Proteome Analysis", *Current Protocols in Protein Science*, Unit 22.1, 2002, 1-19.

(Continued)

*Primary Examiner* — Alex Noguerola

(57) ABSTRACT

The present invention provides methods, compositions, and kits for protein crystallization. The present invention involves electrophoretically focusing at least a first protein species within a matrix comprising at least 2 regions of different pH, the protein being present in amount sufficient to permit crystallization within said pH gradient.

9 Claims, 5 Drawing Sheets

OTHER PUBLICATIONS

De Marcos et al., "An Optical Glucose Biosensor Based on Derived Glucose Oxidase Immobilised Onto a Sol-Gel Matrix", *Sensors and Actuators*, vol. 57, 1999, 227-232.

Garcia-Ruiz, "Crystalization Screening Directly in Electrophoresis Gels", *Journal of Crystal Growth 2001.232*, Abstract and see Experimental procedures, 2001, 596-602.

Gill, "Encapsulation of Biologicals Within Silicate Siloxane, and Hybrid Sol-Gel Polymers: An Efficient and Generic Approach", *Journal of American Chemical Society*, vol. 120, 1998, 8587-8598.

Gill, "Bio-Doped Nanocomposite Polymers: Sol-Gel Bioencapsulates", *Chemistry of Materials*, vol. 13, No. 10, 2001, 3404-3421.

Invitrogen, "Zoom IPGRunner System", *Invitrogen . Zoom IPGRunner System Technical support Notes*.

Pandey, et al., "Reversal in the Kinetics of the M State Decay of D96N Bacteriodopsin: Probing of Enzyme Catalyzed Reactions", *Sensors and Actuators*, vol. 36, Oct. 1, 1996, 470-474.

Perduca, "Crystalisation of Chicken Liver (Basic ) Fatty acid binding protein after publication in Multicompartment Electrolyzers with isoelectric Membranes", *Electrophoresis*, 2000, vol. 21, 2316-2320.

Thorn et al., "A Novel Method of Affinity-Purfying Proteins Using a Bisarsenical Fluorescein.", *Protein Science*, vol. 9, No. 2, Feb. 2000, 213-217.

Zuo et al., "Comprehensive analysis of complex proteomes using microscale solution isoelectrofocusing and slightly overlapping narrow range two-dimensional gels.", *Proteomics*, vol. 2, 2002, 58-68.

Zuo et al., "Comprehensive analysis of complex proteomes using microscale solution isoelectrofocusing prior to narrow pH range two-dimensional electrophoresis", *Analytical Biochemistry*, vol. 284, 2000, 266-278.

Zuo et al., "Enhanced analysis of human breast cancer proteomes using micro-scale solution isoelectrofocusing combined with high resolution 1-D and 2-D gels. Journal of Chromatography", *Journal of ChromatographyB*, vol. 782, 2002, 253-265.

Zuo et al., "Towards global analysis of mammalian proteomes using sample prefractionation prior to narrow pH range two-dimensional gels and using one-dimensional gels for insoluble and large proteins. ", *Electrophoresis*, vol. 22, 2001,1603-1615.

\* cited by examiner

METHODS, COMPOSITIONS, AND KITS FOR PROTEIN CRYSTALLIZATION

CROSS-REFERENCE TO RELATED APPLICATIONS

This application claims the benefit of U.S. provisional patent application Ser. No. 60/525,811 filed Nov. 28, 2003, the disclosure of which is incorporated herein by reference in its entirety.

BACKGROUND OF THE INVENTION

Knowledge of the three dimensional structure of a protein is often necessary in order fully to elucidate its biological function and its interaction with other proteins, and with non-protein cofactors, in a physiological pathway. Knowledge of a protein's 3D structure is critical to the rational design of small chemical entities capable of interacting with the protein with high affinity, a process used both for creation and for optimization of pharmaceutical compounds intended for ultimate use in the clinic.

Although solution phase NMR spectroscopy has shown promise in elucidating protein 3D structure, its use is circumscribed by various technical limitations, and X-ray crystallography remains the principal means by which three dimensional protein structures are determined at the atomic level.

Yet crystallization of proteins remains an inexact and cumbersome art.

Typically, a protein desired to be crystallized is subjected to a wide variety of environmental conditions, including a wide range of solution chemistries, either serially or in a highly parallel series of assays. The large number of assays demands a commensurately large quantity of protein. Positive results occur episodically, and often only after weeks of incubation. Even when a positive result is obtained in the form of a crystal, preparing and mounting the crystal on an x-ray machine can be an arduous, time-consuming process that often results in crystal degradation or even loss.

Thus, there exists a need in the art for a simple, rapid, versatile method of producing protein crystals that neither requires multiple assays, a large amount of protein, nor difficult crystal manipulation methods.

SUMMARY OF THE INVENTION

The present invention solves these and other needs in the art by providing, in a first aspect, a method of crystallizing one or more protein species of interest.

The method comprises electrophoretic focusing of at least a first protein species within a pH gradient, such as a continuous pH gradient, or within a polymer matrix that includes at least 2 regions of different pH, the protein being present in an amount sufficient to permit crystallization within the gradient.

Without intending to be bound by theory, it would appear that as a protein approaches its isoelectric point and thereby becomes more concentrated, the loss of net charge reduces its aqueous solubility, facilitating crystallization. Thus, applied to the gradient in sufficient amount, a protein may be observed to crystallize at or near its isoelectric focal point, particularly when solubilizing and denaturing agents that are typically used in analytical isoelectric focusing (IEF) are omitted during the electrophoretic procedure.

The method does not require that crystallization be effected exactly at the isoelectric point, however. Rather, by exposing the protein to a continuous pH gradient, the method submits the protein in a single procedure to a continuously varying spectrum of environmental conditions as the protein migrates through the pH gradient, at least one of which conditions proves effective at instigating crystallization. The protein crystals created within the pH gradient or the polymer matrix that includes at least 2 regions of different pH, can, in some embodiments, thereafter be used to nucleate further crystallization of the respective protein from solution. In other words, these protein crystals can be used as seed crystals. Therefore, in certain aspects, provided herein is a method of forming seed crystals of one or more protein species of interest.

In a related embodiment, the method comprises electrophoretically transporting at least a first protein species within a pH gradient, such as a continuous pH gradient, or within a polymer matrix that includes at least 2 regions of different pH, wherein the isoelectric point of the protein falls outside of the pH gradient or the pH regions of the polymer matrix, the protein being present in an amount sufficient to permit formation of protein crystals at a terminal region of the pH gradient or polymer matrix.

The method can further include removing the terminal region of the polymer matrix that includes the protein crystals, and analyzing the structure of the proteins in the protein crystals, for example using x-ray diffraction. The method can include using a protein crystal transport tool to transport the protein crystals embedded in the polymer matrix, to an x-ray diffraction holder.

The method is simple, rapid, applicable to a wide variety of proteins, including proteins in an inhomogeneous admixture, and requires minimal user intervention, thus providing significant advantages over methods currently used in the art.

In one series of embodiments, the focusing is conveniently performed in a matrix having an immobilized continuous pH gradient, such as in immobilized pH gradient (IPG) strip.

In another aspect, the invention provides protein crystal compositions created using the methods of the present invention.

In one series of embodiments, the composition comprises at least one crystal of at least a first protein species, and a polymer matrix comprising a plurality of species of pH-conferring moieties, each of the plurality having a distinct pKa. In certain embodiments, the plurality of covalently linked, pH-conferring moieties collectively establish a continuous pH gradient along at least one dimension of the polymeric matrix.

In certain particularly useful embodiments, at least one crystal of the at least first protein species is of sufficient size as to permit X-ray diffraction analysis, and the protein is crystallized in a native, non-denatured, conformation.

The polymer matrix can be an acrylamide polymer, such as an acrylamide polymer comprising a plurality of covalently linked pH-conferring moieties, such as the acrylamide matrix of an IPG strip. At least one of the pH-conferring moieties can, for example, be an acrylamido buffer monomer that is co-polymerized with the acrylamide monomers.

The composition may, in various embodiments, lack detergent in amounts and of composition sufficient to denature the first protein species, thus preserving a native conformation of the crystallized protein. Analogously, the composition may, in various additional embodiments, lack chaotropic agents in amounts and of composition sufficient to denature the first protein species, thus preserving a native conformation of the crystallized protein.

In other words, in such compositions the amounts of detergent or chaotropic agents present, if any, are insufficient to effect denaturation or to stabilize other non-native conformations of the first protein species therein.

In yet a further aspect, the invention provides kits for facilitating the practice of the methods of the present invention.

In one series of embodiments, the kit comprises a polymer matrix that includes at least 2 regions of different pH, such as a polymer matrix having a continuous pH gradient and one or more of instructions for performing the methods of the present invention, a protein crystal transport tool for transporting a crystal embedded gel to an x-ray diffraction holder, and an x-ray crystallography holder.

The kit can further include an aqueous solvating composition, the solvating composition being adapted to and permissive for subsequent crystallization, according to the method of the present invention, of a protein species dissolved therein.

For example, the solvating composition may, in typical embodiments, lack detergent in amounts and of composition sufficient to denature a protein. The solvating composition may typically lack chaotropic agents in amounts and of composition sufficient to denature a protein. The solvating composition will typically be of low ionic strength, and only slightly buffered.

In other words, in such solvating compositions the amounts of detergent or chaotropic agents present, if any, are insufficient to effect denaturation or to stabilize other non-native conformations of the first protein species therein.

To facilitate the crystallization of proteins that may initially be present in compositions that are insufficiently permissive of crystallization according to the methods of the present invention, certain embodiments of the kits of the present invention may include means for exchanging a protein into said aqueous solvating composition.

In a variety of embodiments, the polymer matrix is part of an IPG strip, and the kit comprises one or more IPG strips. In typical embodiments, the kit comprises a selection of IPG strips having different continuous pH ranges, including both linear and nonlinear pH ranges, so as to facilitate the crystallization of a wide variety of proteins of disparate pI.

Usefully, the kit comprises means for effecting isoelectric focusing in IPG strips.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

DETAILED DESCRIPTION

Figure 1:
FIG. 1 is a photomicrograph showing crystals of soybean trypsin inhibitor formed within a pH 4.5-5.5 IPG strip (ZOOM® Strip, Invitrogen Corp., Carlsbad, Calif.) after fewer than 4 hours of isoelectric focusing in an Invitrogen Corporation ZOOM® IPGRunner cassette, according to one embodiment of the methods of the present invention.

In a first aspect, the invention provides a method for crystallizing one or more protein species of interest.

The method comprises electrophoretic focusing of at least a first protein species within a pH gradient, the protein being present in sufficient amount to permit crystallization within the gradient. The protein crystals created within the pH gradient can, in some embodiments, thereafter be used to nucleate further crystallization of the respective protein from solution. Thus, the protein crystals can be used as seed crystals.

Accordingly, in certain aspects of the present invention, provided herein is a method of forming seed crystals of one or more protein species of interest by electrophoretic focusing of at least a first protein species within a pH gradient, the protein being present in sufficient amount to permit crystallization within the gradient, and contacting the protein crystals with additional protein of interest at a concentration sufficient to instigate additional crystal formation from the protein crystals.

Typically, the protein crystals in the pH gradient are transferred to a new vessel in which a solution of the protein of interest is added to form additional crystals using the protein crystals formed in the pH gradient as seed crystals. The protein crystals in the pH gradient are typically isolated before they are transferred to the new vessel for additional crystal formation.

In certain aspects, at least one protein of interest is electrophoretically transported within a polymer matrix that includes at least 2 regions of different pH. In certain aspects, the polymer matrix includes a pH gradient. The pH gradient can be linear or nonlinear, and will typically, although not necessarily, include the isoelectric point of the protein or proteins desired to be crystallized. The pH gradient may be comprised of smooth transitions of pH or pH steps, and the number of steps can be as few as one. For instances in which the isoelectric point of a protein lies outside the gradient's pH range, protein crystals can still form within the polymer matrix in close proximity to one of the electrodes, which is typically a terminal portion of the polymer matrix (e.g., gel), as disclosed herein.

In a related embodiment, the method comprises electrophoretically transporting at least a first protein species within a pH gradient, such as a continuous pH gradient, or within a polymer matrix that includes at least 2 regions of different pH, such as a polymer matrix that includes a continuous or discontinuous pH gradient, wherein the isoelectric point of the protein falls outside of the pH gradient or the pH regions of the polymer matrix, the protein being present in an amount sufficient to permit formation of protein crystals at a terminal region of the polymer matrix, at an electrode that contacts an end of the polymer matrix, and/or at an object that is located between an end of the polymer matrix and an electrode, such as a wick located between an electrode and a gel end. Such a wick is present, for example, when using the ZOOM® IPG Runner (Invitrogen Corp., Carlsbad, Calif.). The method can further include removing the terminal region of the polymer matrix that includes the protein crystals and analyzing the structure of the protein in the protein crystals, for example, using x-ray diffraction. The isoelectric point of the protein falls outside of the pH gradient or the pH regions of the polymer matrix when the isoelectric point of the protein is lower or higher than the lowest and highest pH regions, respectively, of the polymer matrix.

In certain aspects, the method of crystallizing at least one protein provided herein can include using a protein crystal transport tool to excise polymer matrix sections containing protein crystals and to transport the protein crystals embedded in the polymer matrix to an x-ray diffraction holder. Furthermore, the protein crystals can be analyzed using x-ray diffraction or solubilized and analyzed by solution phase NMR.

The gradient can have a pH range of as little as 0.5 pH unit, 1.0 pH unit, 1.5 pH unit, and may have a range of as much as 2 pH units, 3 pH units, 4 pH units, 5 pH units, 6 pH units, even as much as 7, 8, or 9 pH units, with intermediate non-integral ranges permissible.

For example, a wide pH gradient may prove particularly useful in embodiments in which the pI of the protein species desired to be crystallized is unknown, and in embodiments, further described-below, in which the protein species desired to be crystallized is present in inhomogeneous admixture with other protein species with divergent pI values. Conversely, a shallow pH gradient may prove particularly useful in embodiments in which the pI of the protein species desired to be crystallized is precisely known, and in embodiments in which the protein species desired to be crystallized is present in substantially purified form.

The pH gradient can extend as low as pH 1, pH 1.5, even as low as pH 2, although more typically the pH gradient will extend only as low as pH 2.5 or 3, and can extend as high as pH 13, more typically as high as pH 12, and more typically no more than about pH 10, with intermediate and non-integral values permissible.

The isoelectric point of the protein desired to be crystallized may fall in the middle of the pH gradient or towards its acidic or basic end.

Preferably, the isoelectric focusing is performed in a matrix having an immobilized pH gradient.

The matrix can be a polymer matrix.

For example, the matrix can be a polyacrylamide matrix produced by co-polymerization of monoolefinic acrylamide monomers with diolefinic or polyolefinic acrylamide monomers.

Monoolefinic monomers useful in the preparation of polyacrylamide matrices for use in the methods of the present invention include acrylamide, methacrylamide and derivatives thereof such as alkyl derivatives or hydroxyalkyl derivates, e.g. N,N-dimethylacrylamide, N-hydroxypropylacrylamide, and N-hydroxymethylacrylamide. The monoolefinic monomer can also be selected from acrylic and methacrylic acid derivatives, e.g., alkyl esters such as ethyl acrylate and hydroxyalkyl esters such as 2-hydroxyethyl methacrylate.

Diolefinic or polyolefinic cross-linking monomers useful in the preparation of polyacrylamide matrices for use in the methods of the present invention include compounds containing two or more acryl or methacryl groups, such as methylenebisacrylamide, N,N'-diallyltartardiamide, N,N'-1,2-dihydroxyethylene-bisacrylamide, N,N-bisacrylyl cystamine, trisacryloyl-hexahydrotriazine.

In other embodiments, the polymer matrix is prepared by co-polymerization of a monoolefinic acrylamide monomer, such as those described above, with a polysaccharide substituted to contain vinyl groups, for example allyl glycidyl dextran, as described in U.S. Pat. Nos. 4,504,641 and 4,542,200, the disclosures of which are incorporated herein by reference in their entireties. Other containing matrices useful in the methods of the present invention include the covalently cross-linked, mixed-bed agarose polyacrylamide matrices described in U.S. Pat. No. 5,785,832, the disclosure of which is incorporated herein by reference in its entirety.

In various embodiments, the continuous pH gradient is created by the covalent linkage within the polymer matrix of a plurality of species of buffering (synonymously, "pH-conferring") moieties, the various species having disparate pKa values.

In one series of embodiments, the co-polymerized pH-conferring monomer is an acrylamido buffer monomer. As is known in the art, acrylamido buffers are non-amphoteric weak acids and bases having a vinyl moiety for covalent incorporation into the gel matrix.

Acrylamido buffer monomers useful in the polymer matrices for use in the methods of the present invention are known in the art. A number of commercially available acrylamido buffers (Amersham Biosciences, Piscataway, N.J., USA, and Sigma-Aldrich, St. Louis, Mo., USA) include: 2-acrylamido-2-methylpropane sulfonic acid; 2-acrylamidoglycolic acid; N-acryloylglycine; 4-acrylamidobutyric acid; 2-morpholinoethylacrylamide; 3-morpholinopropylacrylamide; N,N-dimethylaminoethylacrylamide; N,N-dimethylaminoethylpropylacrylamide; and N,N-diethylaminopropylacrylamide.

In other embodiments, the co-polymerized pH-conferring monomer is a dicarboxylic acid, usefully with the formula

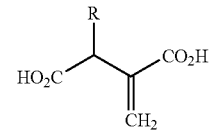

in which R is selected from the group consisting of: —H, —OH, —CH$_2$OH, —CO$_2$H, —NHR', —OCH$_3$, and —NR'R", —Cl, —F, —I, and wherein R' and R" are each independently selected from the group consisting of —CH$_3$, —CH$_2$CH$_3$, —CH$_2$OH, —CH$_2$CH$_2$OH, —CH$_2$CH$_2$CH$_3$.

In certain embodiments, the polymer matrix is adherent to at least one solid backing member. Adherence can be by covalent linkage to a single backing member, which can usefully be made of a flexible plastic having pendent vinyl groups.

In a subset of such embodiments, the plastic backing member is fashioned in the shape of a strip that is greater in length along the axis of the pH gradient than in the dimensions orthogonal thereto.

The strip can, for example, have approximate lengths along the axis of the pH gradient of, for example, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 180 mm, 200 mm, 220 mm, 240 mm, or even longer, with intermediate lengths permissible.

Longer strips can present advantages in resolving, and crystallizing, a protein species present in inhomogeneous admixture with a large number of other proteins. For example, a pH gradient embodied on a longer strip may provide isoelectric focusing at a higher resolution. Such a higher resolution may be particularly useful when formation of protein crystals is particularly sensitive to the pH environment. Shorter strips can present advantages in speed of focusing and crystallization.

In some embodiments, the strips can have approximate widths of, for example, 1.0 mm, 1.5 mm, 2 mm, 2.5 mm, 3 mm, 3.5 mm, 4 mm, 4.5 mm, 5 mm, or even wider and approximate thicknesses of 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm or even thicker, with intermediate lengths permissible.

More narrow strips can present advantages in embodiments in which protein is limited in amount.

In typical embodiments, further described below, IPG strips useful in the methods of the present invention can be provided in dehydrated form, to be rehydrated prior to electrophoretic focusing of proteins therein. Neither complete removal of moisture, during dehydration, nor complete saturation with liquid, during rehydration, is required or intended.

Such immobilized pH gradient (IPG) strips can be cast using methods well known in the art. IPG strips useful in the methods of the present invention are also available commercially in a variety of lengths and pH ranges, typically in such dehydrated form.

For example, ZOOM® Strips from Invitrogen Corporation (Carlsbad, Calif.) are 7 cm long and are available in a pH 3-10 nonlinear range, a pH 4-7 linear range, a pH 6-10 linear range, a pH 4.5-5.5 linear range, a pH 5.3-6.3 linear range, and a pH 6.1-7.1 linear range.

ReadyStrip IPG Strips from Bio-Rad (Hercules, Calif.) are available in lengths of 7 cm, 17 cm, and 18 cm, in pH ranges of pH 3-10, pH 6.3-8.3, pH 3-6, pH 3.9-5.1, pH 4-7, pH 4.7-5.9, pH 5-8, pH 5.5-6.7, pH 7-10, and in a nonlinear range of pH 3-10.

Additionally, Amersham Biosciences (Piscataway, N.J.) sells IPG strips in 7, 11, 13 and 18 cm lengths with pH ranges of pH 4-7, pH 3-10 linear, pH 3-10 nonlinear, and pH 6-11.

In presently preferred embodiments, the IPG strips are formulated to permit rehydration at room temperature in no more than about 8 hours, preferably no more than about 7 hours, 6 hours, 5 hours, 4 hours, even more preferably no more than about 3, 2, or even 1 hour.

Such rapidly rehydratable IPG strips are typically cast from a basic solution and an acidic solution, the basic solution comprising at least three acrylamido buffers with a combined concentration of at least about 32 mM, at least about 35 mM, even at least about 40 mM or more, as further described in commonly owned U.S. provisional patent application Nos. 60/509,512, filed Oct. 7, 2003, 60/510,674, filed Oct. 9, 2003, and commonly-owned and co-pending U.S. patent application Ser. No. 10/961,308, filed Oct. 7, 2004, the disclosures of which are incorporated herein by reference in their entireties.

Although IPG strips, including commercially available IPG strips, provide convenience in the practice of the methods of the present invention, they are not required. The methods of the present invention can be practiced in slab gels, with or without one or more solid support backings, in tubes that can readily be opened, in capillaries, and in any other geometry as may permit isoelectric focusing in a continuous pH gradient.

Because isoelectric focusing in a pH gradient separates proteins based upon differences in their isoelectric points, the protein species desired to be crystallized using the methods of the present invention need not be pure, and may indeed be present in inhomogeneous admixture with at least one additional protein species having a different isoelectric point, a major advantage of the methods of the present invention over methods currently used in the art. In some embodiments, it may also be desirable to crystallize one or more of the additional protein species; in some of these embodiments, each of the protein species can be concurrently crystallized within the continuous pH gradient at its respective isoelectric point.

In some embodiments of the present invention, the nondenaturing conditions may allow protein complexes to preserve their quaternary structure, and thus the components of the complex may not separate under the conditions used in the present invention. Under such conditions, isoelectric focusing of a protein complex using the methods of the present invention may permit crystallization of the protein complex at a particular pH value in the pH gradient.

The proteins desired to be crystallized may, therefore, be initially present within a cell lysate.

The first and optional additional protein species may, for example, be proteins naturally expressed within a cell and be present within a lysate thereof.

Alternatively, the first and optional additional protein species desired to be crystallized may be recombinantly expressed proteins. In such embodiments, the recombinant expression can be effected within a cell, such as a cell selected from the group consisting of: animal cell, including mammalian cell, such as CHO cell; fungal cell, such as a *Saccharomyces cerevisiae* cell or *Pichia* cell; an insect cell; a plant cell; and a prokaryotic cell, such as a eubacterial cell, such as an *E. coli* cell.

In yet another alternative, the first and optional additional protein species desired to be crystallized may be recombinantly expressed within one or more cell-free lysates, such as a coupled transcription-translation system, such as the commercially available ExpressWay coupled transcription-translation system (Invitrogen Corp., Carlsbad, Calif.).

IPG sample preparation solutions used in the art for analysis of proteins typically include one or more denaturing agents, such as urea or thiourea, one or more nonionic or zwitterionic detergents, such as CHAPS, NP-40, CHAPSO, and detergent sulfobetaines such as SB3-10, one or more reducing agents, such as dithiothreitol (DTT) or dithioerythritol (DTE), and carrier ampholytes.

In embodiments of the methods of the present invention in which proteins are desired to be crystallized in their native state—for example, in order subsequently to determine their native 3D structure—denaturing agents and reducing agents are usefully omitted, both from the protein sample applied to the continuous pH gradient and, in embodiments if which the pH gradient is present within an IPG strip, usefully omitted from the strip rehydration solution as well.

Analogously, in embodiments of the methods of the present invention in which proteins are desired to be crystallized in their native state, carrier ampholytes, which tend to adhere to proteins, can usefully be omitted from the protein sample applied to the continuous pH gradient and, in embodiments in which the pH gradient is present within an IPG strip, usefully omitted from the strip rehydration solution as well.

And in embodiments in which proteins do not readily crystallize within the continuous pH gradient, solubilizing agents such as detergents can usefully be omitted from the protein sample applied to the continuous pH gradient and, in embodiments in which the pH gradient is present within an IPG strip, usefully omitted from the strip rehydration solution as well.

If proteins desired to be crystallized according to the methods of the present invention are present in a composition having one or more undesired agents, such as salts or detergents, the protein can be exchanged into a desired solution composition prior to its application to the continuous pH gradient using art-accepted techniques such as dialysis or, as described in Example 3, below, centrifugation using a semipermeable membrane with known molecular weight cutoff.

Thus, in some embodiments of the methods of the present invention, the first and optional additional protein species desired to be crystallized are electrophoretically focused in the substantial absence of detergent. In some embodiments, the first and optional additional protein species are electrophoretically focused in the substantial absence of chaotropes.

In some embodiments, the protein can even be dissolved in, and thus focused in, deionized water, as shown in Example 1, below.

Conversely, agents desired to be present can be added before the application of the proteins to the continuous pH gradient.

For example, non-detergent zwitterions, such as non-detergent sulfobetaines, can be added. Such non-detergent sulfobetaines include, for example, dimethylethylammonium propane sulfonate; 3-(1-pyridino)-1-propane sulfonate; dimethylbenzylammonium propane sulfonate; 3-(4-tert-butyl-1-pyridino)-1-propane sulfonate; and 3-(1-methylpiperidinium)-1-propane sulfonate.

In other embodiments, volume-excluding or macromolecular crowding agents that further concentrate the proteins can be added, additionally or in the alternative. For example, polyethylene glycols or other polysaccharides can be added.

In embodiments of the methods of the present invention in which the continuous pH gradient is immobilized within an IPG strip, electrophoretic focusing of the proteins can usefully be performed by hydratingly lodging the prior-cast, dehydrated, IPG strip within an enclosing member that permits spaced electrical communication with the strip, and then using the spaced electrical communication to establish a voltage gradient in the gel matrix of the strip that is sufficient to effect electrophoretic focusing of proteins therein.

In these embodiments, the method will typically further comprise inserting the IPG strip in its dehydrated state within the enclosing member, and then contacting the enclosed dehydrated IPG strip with an aqueous solution for a time sufficient to lodge the strip within the enclosing member. The aqueous solution used to rehydrate the strip can usefully comprise the first and optional additional protein species to be crystallized.

Such embodiments of the methods of the present invention are readily practiced using the IPGRunner system commercially available from Invitrogen Corp. (Carlsbad, Calif.), which provides means for enclosing a plurality of IPG strips, the enclosing means permitting spaced electrical communication separately with each of the enclosed strips through respective first and second entries. The system further provides means responsive to an external compressive force for effecting spaced electrical communication by a single anode and single cathode simultaneously with each of the enclosed strips, wherein the electrical communication means is capable of distributing an external compressive force to urge the anode and the cathode toward the enclosing means with greater pressure at the first and second entries than elsewhere on the enclosing means.

Advantageously, the IPGRunner system obviates the use of oil, contact to which may interfere with crystallization of subsequent isolation of crystals formed within the strips. Additionally, the IPG strips, with crystals formed therein, can be frozen within the cassette.

Variants of such system prove useful in other embodiments of the present invention. For example, in certain variants, the enclosing member encloses a single IPG strip, rather than a plurality of such strips.

Particularly using the IPGRunner system and its variants (although not limited thereto), the methods of the present invention allow the first and optional additional protein species to be crystallized in fewer than 10 hours, 9 hours, 8 hours, 7 hours, 6 hours, 5 hours, even as few as 4 hours, 3 hours, and even as few as 2 or 1.5 hours, as demonstrated in Examples 1-3 herein below, with intermediate and non-integral values achievable. The rapidity and simplicity with which the protein species desired to be crystallized is exposed to a continuous gradient of environmental conditions, and thus crystallized, presents significant advantages over methods currently used in the art.

The methods of the present invention can be practiced at room temperature or, depending upon the protein desired to be crystallized, at other temperatures. For example, the proteins can be electrophoretically focused at 4° C., 10° C., 15° C., even 20° C., 25° C., even 30° C. or more, with intermediate and non-integral values permissible and with colder temperatures facilitating crystallization of certain proteins.

Although the methods of the present invention permit a desired protein species to be purified and crystallized in a single step from an inhomogeneous mixture, in some embodiments the method may further comprise an antecedent purification step, typically one in which the first and optional additional protein species desired to be crystallized are partially purified from an inhomogeneous protein mixture.

Prior purification can be effected by any means known in the art.

For example, the protein species desired to be crystallized may be partially purified before isoelectric focusing by one or more well known chromatographic or electrophoretic methods, including gel filtration, ion exchange, reverse phase HPLC, or capillary or capillary zone electrophoresis. The protein species desired to be crystallized may in addition or in the alternative be size fractionated by dialysis or by centrifugation through columns having semi-permeable membranes.

Recombinant proteins desired to be crystallized according to the methods of the present invention may additionally or in the alternative be partially or completely purified before isoelectric focusing fused affinity tags, such as the 6×His tag, myc tag, FLAG tag, or tetracysteine tag (CCXXCC, where "X" represents any amino acid except cysteine). Tetracysteine-tagged fusion proteins can be purified using biarsenical affinity supports, such as the FlAsH™ (LUMIO™ green) affinity resin described in *Protein Sci.* 9:213-21.7 (2002), and further described in commonly-owned and co-pending U.S. application Ser. No. 10/971,606, filed Oct. 22, 2004, the disclosures of which are incorporated herein by reference in their entireties. In such embodiments, the biarsenical compound does not need to be a biarsenical derivative of a fluorophore; it can be any biarsenical with spacing suitable for binding to a tetracysteine motif.

In certain pre-purification embodiments of the methods of the present invention, the protein species desired to be crystallized is first partially purified by solution phase isoelectric focusing fractionation. See Zuo et al., *Anal. Biochem.* 284: 266-278 (2000); Zuo et. al., *Electrophoresis* 22: 1603-1615 (2001); Zuo et al., *Proteomics:* 2: 58-68 (2002); Zuo et al., *Journal of Chromatography B* 782: 253-265 (2002); Ali-Khan et al., *Current Protocols in Protein Science* 22.1: 1-19 (2002), the disclosures of which are incorporated herein by reference in their entireties. Devices and kits for fluid phase isoelectric focusing are available commercially (ZOOM™ IEF Fractionator, Invitrogen Corp., Carlsbad, Calif.).

Proteins crystallized according to the methods of the present invention, whether crystallized directly or only after prior partial purification, may thereafter be isolated from the continuous pH gradient.

In embodiments in which the pH gradient is fixed within a polymer matrix, as in the polyacrylamide gel of an IPG strip, the portion of the polymer matrix comprising the protein crystals can be mechanically excised. This mechanical excision can be performed, for example, using one or more protein crystal transport tools disclosed herein. In embodiments in which a plurality of protein species are concurrently crystallized within a single polymer matrix, each such crystallized protein species can be separately excised there from. In some embodiments, the excised protein crystals can thereafter be washed with a solvent that supports maintenance of the crystal structure.

The protein crystals created within the continuous pH gradient can, in some embodiments, thereafter be used to nucleate further crystallization of the respective protein from solution, as demonstrated in Example 2, below.

The crystals, whether obtained directly from the continuous pH gradient or from a solution seeded with crystals so obtained, are in many embodiments of the methods of the present invention thereafter submitted to analysis, typically, but not exclusively, analysis to determine the 3D structure of the crystallized protein.

Analysis may, for example, comprise diffraction analysis, such as X-ray diffraction analysis, including, e.g., X-ray diffraction analyses using third-generation synchrotron sources, undulator beam lines, multi-wavelength anomalous dispersion (MAD) data collection, and CCD detection.

In some embodiments, the crystals will be cryo-protected, for example by flash cooling and storage at cryogenic temperatures before analysis. For example, the crystal can be mounted into a cryo-loop, flash cooled at liquid nitrogen temperature, and subsequently stored in liquid nitrogen. In certain aspects in which the protein crystals are formed in a polymer matrix having an immobilized pH gradient, such as an isoelectric focusing gel or an IPG strip, one or more pieces of the polymer matrix that include the protein crystals are dried and directly analyzed by X-ray crystallography. For example, the polymer matrix pieces can be placed onto a cryo-loop for direct x-ray crystallographic analysis. The polymer matrix with the protein crystals can be dried/stored at room temperature until direct x-ray crystallographic analysis.

In some embodiments, the first (and optional additional protein species) desired to be crystallized is crystallized as part of a complex, such as a complex with a compound chosen from a chemical library; in such embodiments, the protein species desired to be crystallized are first complexed, and then subjected to isoelectric focusing in a continuous pH gradient.

Analysis may, in addition or in the alternative, include nuclear magnetic resonance spectroscopy and/or scanning electron microscopy.

In another aspect, the invention provides protein crystal compositions created using the methods of the present invention.

In a first series of embodiments, the composition comprises at least one crystal of at least a first protein species, and a polymer matrix comprising a plurality of species of pH-conferring moieties, each of the plurality having a distinct pKa. The at least one protein crystal is typically embedded within the polymer matrix.

In certain embodiments, at least one crystal of the at least first protein species is of sufficient size as to be light microscopically observable. In particularly useful embodiments, at least one crystal of the at least first protein species is of sufficient size as to permit X-ray diffraction analysis.

The protein crystal is usefully a crystal of the protein in a native, non-denatured, conformation. The native, non-denatured, conformation can, for example, be a conformation of the protein alone. In other embodiments, the native, non-denatured, conformation can be the conformation of the protein complexed with a non-protein ligand, such as a natural cofactor or a mimetic thereof. In yet other embodiments, the native, non-denatured, conformation can be the conformation of the protein complexed with another protein species.

As described above with respect to the methods of the present invention, the polymer matrix can be an acrylamide polymer, such as an acrylamide polymer comprising a plurality of covalently linked pH-conferring moieties, each of the plurality of species having a distinct pKa values.

In certain embodiments, the plurality of covalently linked pH-conferring moieties collectively establish a continuous pH gradient along at least one dimension of the polymeric matrix.

At least one of the pH-conferring moieties can, for example, be an acrylamido buffer monomer that is co-polymerized with the acrylamide monomers. In some embodiments, each of the plurality of pH-conferring moieties is an acrylamido monomer.

The acrylamido monomers can be selected, for example, from the group consisting of 2-acrylamido-2-methylpropane sulfonic acid; 2-acrylamidoglycolic acid; N-acryloylglycine; 4-acrylamidobutyric acid; 2-morpholinoethylacrylamide; 3-morpholino-propylacrylamide; N,N-dimethylaminoethylacrylamide; N,N-dimethylaminoethylpropylacrylamide; and N,N-diethylaminopropylacrylamide.

The polymer matrix can be adherent to at least one support backing, usefully covalently attached to a single support backing. In certain IPG strip embodiments, the support backing is a flexible plastic fashioned as a strip having greater length in the axis of the pH gradient than in directions orthogonal thereto.

The pH gradient within the polymer matrix can have a pH range of up to 12 pH units, although typically the pH range, as in commercial IPG strips, will be no more than about 7, 8, 9, or 10 pH units. Conversely, the gradient can have a pH range of as little as 0.5 pH units, although ranges of at least 1 pH unit will be more typical.

The composition will, in various embodiments, lack detergent in amounts and of composition sufficient to denature the first protein species, thus preserving a native conformation of the crystallized protein. Although these embodiments comprehend compositions completely lacking in detergent, other such embodiments include one or more detergents in amounts and of composition that do not effectuate denaturation of the first protein species.

Analogously, the composition will, in various embodiments, lack chaotropic agents in amounts and of composition sufficient to denature the first protein species, thus preserving a native conformation of the crystallized protein. Although these embodiments comprehend compositions completely lacking in chaotropic agents, other such embodiments include one or more chaotropes in amounts and of composition that do not effectuate denaturation of the first protein species.

The compositions may further comprise a non-detergent zwitterion, such as a non-detergent sulfobetaine. Such non-detergent sulfobetaines include, for example, dimethylethylammonium propane sulfonate; 3-(1-pyridino)-1-propane sulfonate; dimethylbenzylammonium propane sulfonate; 3-(4-tert-butyl-1-pyridino)-1-propane sulfonate; and 3-(1-methylpiperidinium)-1-propane sulfonate.

In other embodiments, the compositions comprise volume-excluding or crowding agents such as polyethylene glycols, monosaccharides, or other polysaccharides.

In yet further embodiments, the composition may further comprise at least one crystal of at least second protein species, spatially segregated from at least one crystal of the first protein species. As in the compositions comprising one or more crystals of a single protein species, in some embodiments at least one of the crystals of the at least second protein species is of a size sufficient to be observed by light microscope; and in some embodiments, at least one of the crystals of the at least second protein species is of sufficient size to permit X-ray diffraction analysis.

In some embodiments, the compositions of the present invention are frozen.

In yet a further aspect, the invention provides methods for selling polymer matrices and tools for practicing the methods provided herein. In a first series of embodiments, the method includes providing a means, typically an Internet based means, for linking the ordering of a polymer matrix having at least 2 regions of different pH, such as a continuous pH gradient, with ordering one or more x-ray diffraction holders and/or ordering one or more tools for excising and transporting a portion of the polymer matrix, such as one or more protein crystal transport tools for transporting a crystal-embedded polymer matrix section to an x-ray diffraction holder, as disclosed herein. For example, when a customer is directed to an Internet page with a picture and/or description of a polymer matrix with at least 2 regions of different pH, or when a customer uses an on-line or phone-based means to order a polymer matrix with at least 2 regions of different pH, the customer is offered over the telephone, or presented with an Internet link to purchase one or more protein crystal transport tools and/or one or more x-ray crystallography holders. In another aspect, provided herein is a fee-based service for performing the methods disclosed herein.

In yet a further aspect, the invention provides kits for facilitating the practice of the methods of the present invention.

In a first series of embodiments the kit comprises a polymer matrix having a continuous pH gradient and instructions for performing the methods of the present invention. In addition, the kit can include a means for excising and transporting a portion of the polymer matrix, such as one or more protein crystal transport tools for transporting a crystal-embedded gel piece to an x-ray diffraction holder. The one or more protein crystal transport tools represent another aspect of the invention. In certain aspects, the polymer matrix includes a backing and is an IPG strip.

The protein crystal transport tool(s) is typically used to cut away or otherwise remove from the remainder of the polymer matrix, a portion of the polymer matrix that includes the protein crystals to a size appropriate for an x-ray diffraction holder. The protein crystal transport tool is then used to transport the cut portion of polymer matrix that includes the protein crystals to an x-ray diffraction holder. The protein crystal transport tool can also be used, in certain embodiments, to separate the gel matrix from a backing material. In certain aspects, several protein crystal transport tools are used to achieve these functions. For example, one tool can function as a cutter and another tool can function to pick up the cut portion and transfer it to the x-ray diffraction holder. The tools may include a single handle or shaft that can be used interchangeably on a series of tips that perform the various functions.

The protein crystal transport tool has a polymer matrix contact portion and can also include a handle or shaft in addition to the polymer matrix contact portion. As will be understood, the tool can take on any shape or size to achieve the functions stated above. For example, the protein crystal transport tool can take the general shape of a miniaturized spade, knife, spatula, scraper, probe, chisel, shovel, scooper, or hoe, or can be a circular or cylindrical bore-type cutting tool that "punches out" a region of the polymer matrix that includes the protein crystals, similar in shape to micro tools known in the art of protein crystal manipulation (See, for example, Micro Tools™ available from Hampton Research, Aliso Viejo, Calif.).

The protein crystal transport tool can be made of any material that is suitable for cutting and transporting a polymer matrix without damaging protein crystals. For example, all or at least the polymer matrix contact region of the gel transport tool can made of a materials that are known for crystal transport, such as steel, for example stainless steel, or hardened tungsten steel. The handle or shaft, can be made of the same or a different materials than the polymer matrix contact region. For example, the handle can be made of a material such as aluminum.

In certain aspects, the dimensions of the tools are greater than those used in protein crystal manipulation and smaller than tools used to excise gel portions for other purposes. The protein crystal transport tool is typically capable of cutting the polymer matrix in a manner that is precise enough to remove a small section of a thin polymer matrix (e.g., a section that is about 1-5 mm in width, about 1-5 mm in length, and about 1-5 mm in thickness), and in certain aspects is used to scrape a cut polymer matrix from a backing strip. In embodiments where the polymer matrix is attached to a backing, such as where IPG strips are used, the tool is typically rigid such that it slides along the stripping backing to lift the gel from the backing. The tool typically includes one or more cutting edges that in certain illustrative embodiments are between 0.5 and 10 mm in length when the cutting edge is a straight edge. In aspects where the tool has a straight cutting edge, the tool can also include a surface that is rectangular in shape. This surface is used to pick up and transport the gel piece, and therefore is typically flat or funneled toward a center portion. The area of this surface is typically between 5 $mm^2$ and 100 $mm^2$, and in certain illustrative examples is between 10 $mm^2$ and 50 $mm^2$.

Where the tool is a bore-type cutting device the cutting edge typically is capable of cutting a section of the gel that has an area of between 5 mm and 100 mm, or in certain illustrative examples between 10 mm and 50 mm. The bore-type cutting instrument can be used at the end of a capillary tube, which is used to collect and transport an excised portion of gel.

In embodiments, where the tool is a spatula-type tool, the front edge of the polymer matrix contact surface of the protein crystal transport tool can be the longest edge of the polymer matrix contact surface and should be no more than 100 mm wide. In illustrative examples, the width of the front edge is 50, 25, 20, 10, 9, 8, 7, 6, 5, 4, 3, 2, 1, 0.9, 0.8, 0.7, 0.6, 0.5, 0.4, 0.3, 0.2, or 0.1 mm. For example, the width of the front edge of the polymer matrix contact surface of the protein crystal transport tool, in certain illustrative examples, is between 0.1 mm and 10 mm. The other edges of the polymer matrix contact surface in spatula-type embodiments, typically have a width of 10,000, 5000, 2500, 1000, 500, 250, 100, 50, 25, 20, 10, 9, 8, 7, 6, 5, 4, 3, 2, 1, 0.9, 0.8, 0.7, 0.6, 0.5, 0.4, 0.3, 0.2, or 0.1 mm. In certain aspects, the polymer matrix contact surface of a spatula-type tool has an area between 0.1 mm and 10 $cm^2$, 0.5 $mm^2$ and 1 $cm^2$, or in an illustrative example, between 1 $mm^2$ and 100 $mm^2$.

The polymer matrix contact portion can include one surface, two surfaces that angle into contact with one another along a side edge or, for example, can include a bottom wall with two abutting side walls that are vertical with respect to the bottom wall, can be cylindrical in shape, or can include various other configurations that can function as discussed herein. The portion of the tool that is used to transport the section of polymer matrix typically includes at least one surface that is substantially horizontal, or horizontal, or includes a cylindrical cavity for holding a polymer matrix. Thus, the polymer matrix contact portion can be used to hold an excised portion of a polymer matrix on its top surface or within its body. The polymer matrix contact portion when part of a spatula-type tool, when used to transport a portion of a polymer matrix, holds the gel matrix in a position that is substantially parallel to the ground such that the polymer matrix does not fall from the protein crystal transport tool.

In certain embodiments, one or more x-ray diffraction holders are included in the kit. The x-ray diffraction holders can be virtually any type of x-ray diffraction holder known in the art. For example, the x-ray diffraction holder can be a cryo-loop. Furthermore, the x-ray diffraction holder can be made of any suitable material, for example nylon. Accordingly, in certain embodiments, the kit includes a population of nylon fiber loops, such as cryo-loops. The number of x-ray diffraction holders included in the kit can be approximately equal (+/−2) or equal to the number of polymer matrices included in the kit. The x-ray diffraction holders in the kit are typically not reusable.

The kit can include an aqueous solvating composition, the solvating composition being adapted to and permissive for subsequent crystallization, according to the method of the present invention, of a protein species dissolved therein.

For example, the solvating composition will, in typical embodiments, lack detergent in amounts and of composition sufficient to denature a protein. The solvating composition will typically lack chaotropic agents in amounts and of composition sufficient to denature a protein. The solvating composition will typically be of low ionic strength, and only slightly buffered.

In some embodiments, the solvating composition will further comprise a non-detergent zwitterion, such as a non-detergent sulfobetaine, such as a sulfobetaine selected from the group consisting of: dimethylethylammonium propane sulfonate; 3-(1-pyridino)-1-propane sulfonate; dimethylbenzylammonium propane sulfonate; 3-(4-tert-butyl-1-pyridino)-1-propane sulfonate; and 3-(1-methylpiperidinium)-1-propane sulfonate.

To facilitate the crystallization of proteins that may initially be present in compositions that are insufficiently permissive of crystallization according to the methods of the present invention, certain embodiments of the kits of the present invention may include means for exchanging a protein into said aqueous solvating composition.

The exchange means can, for example, be a centrifugation spin column with a semi-permeable membrane having a molecular weight cutoff below the size of proteins desired to be crystallized. In some embodiments, the kit can include a plurality of exchange means, such as spin columns, each of the plurality having a semi-permeable membrane with a different molecular weight cutoff, so as to optimize retention of the desired protein and passage of contaminants.

In a variety of embodiments, the polymer matrix is part of an IPG strip, and the kit comprises one or more IPG strips. In typical embodiments, the kit comprises a selection of IPG strips having different continuous pH ranges, including both linear and nonlinear pH ranges, so as to facilitate the crystallization of a wide variety of proteins of disparate pI.

Usefully, the kit comprises means for effecting isoelectric focusing in IPG strips.

Thus, the kit may usefully further comprise means for enclosing at least one IPG strip, wherein the enclosing means permits spaced electrical communication separately with each of the at least one enclosed strips through respective first and second entries. In some embodiments, the enclosing means is capable of separately enclosing a plurality of IPG strips, permitting spaced electrical communication separately with each of the plurality of enclosed strips.

Conveniently, such kits can further comprise means responsive to an external compressive force for effecting spaced electrical communication by a single anode and single cathode simultaneously with each of the at least one enclosed strips, wherein the electrical communication means is capable of distributing an external compressive force to urge the anode and the cathode toward the enclosing means with greater pressure at the first and second entries than elsewhere on the enclosing means.

The kit may further comprise an electrophoresis tank, the tank dimensioned to accommodate both the means for enclosing IPG strips and the electrical communication means, colloquially denominated a buffer core.

The kits may also comprise means for excising a protein crystal from the polymer matrix, such as a coring tool.

The following examples are offered by way of illustration only, and not by way of limitation.

Example 1

IPG Isoelectric Focusing Crystallization of Soybean Trypsin Inhibitor

Soybean trypsin inhibitor was purchased from Sigma-Aldrich and dissolved in deionized water to a concentration of 10 mg/mL. An aliquot of 150 µL of this solution was used to rehydrate a pH 4.5 to pH 5.5 ZOOM® Strip (Invitrogen Corp., Carlsbad, Calif.) in a ZOOM® IPGRunner cassette (Invitrogen Corp., Carlsbad, Calif.) for 2 hours.

The ZOOM® IPGRunner cassette was thereafter handled essentially according to manufacturer's instructions (including removal of well-forming members, application of wicks, and contact to an IPGRunner buffer core within an electrophoresis tank, all from Invitrogen Corp., Carlsbad, Calif.) and voltage applied as follows: 175V for 15 min, followed by a ramp from 175 to 2000V over the course of one hour, and then 2000V for 2 hours 15 minutes.

Strips were removed from the cassette and examined microscopically. Crystals of soybean trypsin inhibitor were observed in the gel matrix, as shown in FIG. 1.

Example 2

IPG Isoelectric Focusing Preparation of Seed Crystals

Lysozyme was purchased from Sigma-Aldrich and dissolved in deionized water at a concentration of 3 mg/mL. An aliquot of 150 microliters was used to rehydrate a pH 9-12 IPG strip (prepared in-house) within an Invitrogen ZOOM® IPGRunner cassette for 1 hour.

The ZOOM® IPGRunner cassette was thereafter handled essentially according to manufacturer's instructions (including removal of well-forming members, application of wicks, and contact to an IPGRunner buffer core within an electrophoresis tank, all from Invitrogen Corp., Carlsbad, Calif.) and voltage applied using the following step voltage protocol: 175 volts for 15 minutes and 500 volts for 2 hours.

Figure 2A:
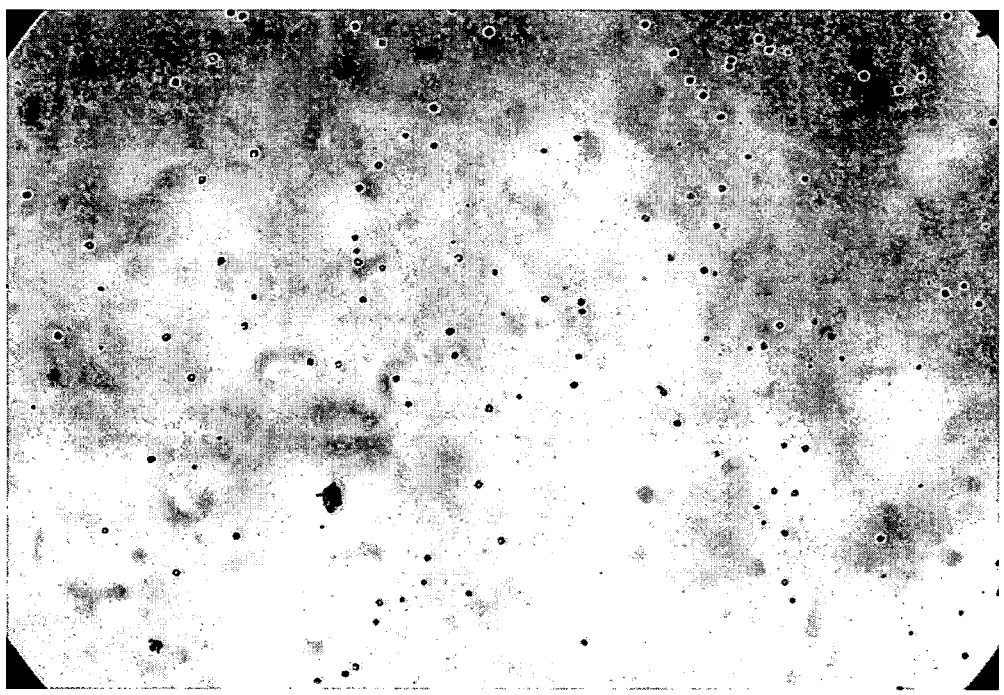
FIG. 2A is a photomicrograph showing seed crystals of lysozyme formed within a pH 9-12 IPG strip after fewer than 3 hours isoelectric focusing in a ZOOM® IPGRunner cassette (Invitrogen Corp., Carlsbad, Calif.)

The strip was removed and examined microscopically. Micro-crystals of lysozyme were observed in the gel strip, as shown in FIG. 2A.

A section of the strip containing the micro-crystals was placed into a test tube containing a 22 mg/ml solution of lysozyme; at this concentration, lysozyme will not spontaneously crystallize within the tube.

Figure 2B:
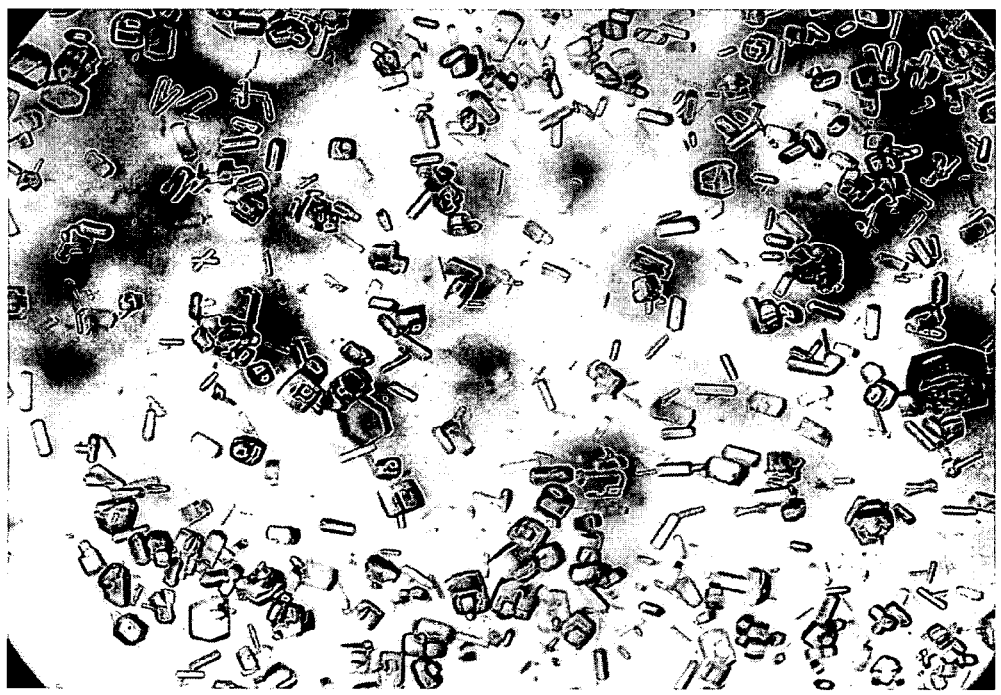
FIG. 2B is a photomicrograph of crystals of lysozyme grown from these initial seeds, according to one embodiment of the present invention.

After two days at room temperature, the strip was removed from the tube and examined microscopically: large crystals with similar morphology were observed as shown in FIG. 2B.

Example 3

IPG IEF Crystallization After Buffer Exchange

Cytochrome P450 3A4 in a buffer containing 20 mM $K_2PO_4$, 0.2 mM EDTA, 1 mM DTT, and 20% glycerol (PanVera Division of Invitrogen Corp.) was subjected to solution exchange into 0.3 mM CHAPS/0.3 mM octyl-β-D-1-thioglucopyranoside (OTGP) using a Centricon (YM-10) 10 kDa cutoff centrifuge tube from Millipore (Billerica, Mass.).

A pH 3-10 non-linear ZOOM® Strip (Invitrogen Corp., Carlsbad, Calif.) was rehydrated in the ZOOM® IPGRunner cassette for 1 hour with a volume of 150 µL of 0.1 mg/mL of cytochrome P450 3A4 in the CHAPS/OTGP solution. Electrode wicks were wetted with 0.3 mM CHAPS/0.3 mM OTGP and applied to the cassette, essentially as per manufacturer's instructions.

Figure 3:
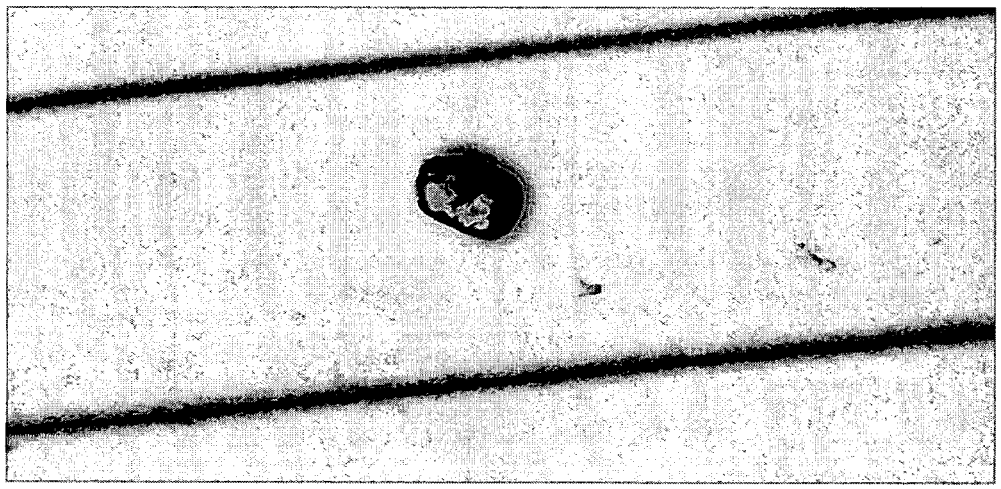
FIG. 3 is a photomicrograph showing a capillary-mounted crystal of cytochrome P450 3A4. This crystal was produced within a pH 3-10 non-linear IPG strip (ZOOM® Strip, Invitrogen Corp., Carlsbad, Calif.) after 1 hour of isoelectric focusing in a ZOOM® IPGRunner cassette (Invitrogen Corp., Carlsbad, Calif.), according to one embodiment of the present invention.

The cassette was placed in the IPGRunner apparatus and run with an applied voltage of 200 volts for 1 hour. The strips were removed and examined microscopically. Crystals observed in the gel strip were mounted in thin-walled glass capillary tubes (0.7 mm in diameter) for x-ray crystallographic analysis. One such capillary-mounted crystal with which x-ray diffraction images were collected is shown in FIG. 3. The crystals appeared brown in color to the naked eye during and after isoelectric focusing without the use of a microscope, which provides evidence of the expected presence of native, non-denatured, concentrated, ligand-containing protein.

Example 4

IPG IEF Crystallization Under an Electrode

Hemoglobin S was purchased from Sigma-Aldrich and dissolved in dilute (0.125×) IEF Cathode Buffer (Invitrogen Corp., Carlsbad, Calif.) to a concentration of 1 mg/mL. An aliquot of 150 µL of this solution was used to rehydrate a pH 9-12 IPG strip (prepared in-house) within an Invitrogen ZOOM® IPGRunner cassette (Invitrogen Corp., Carlsbad, Calif.) for 1 hour.

The IPGRunner cassette was thereafter handled essentially according to manufacturer's instructions (including removal of well-forming members, application of wicks, and contact to an IPGRunner buffer core within an electrophoresis tank, all from Invitrogen Corp., Carlsbad, Calif.) with a constant voltage of 200 Volts applied for 4 hours to effect electrophoretic crystallization.

Figure 4:
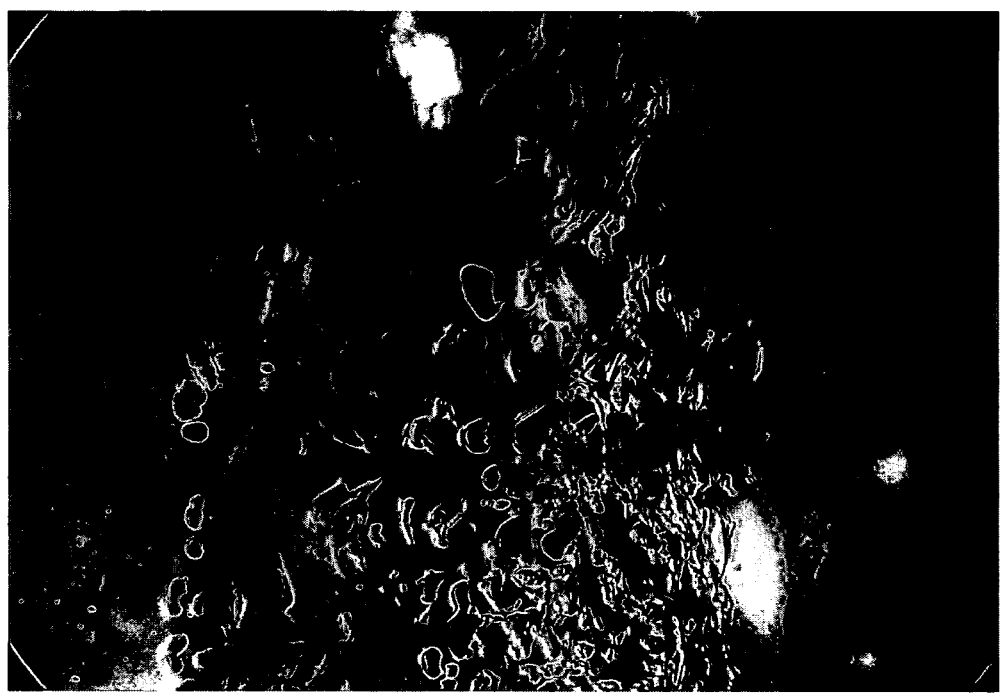
FIG. 4 is a photomicrograph showing crystals of Hemoglobin S formed under the electrode at the acidic end of a pH 9-12 IPG Strip after 4 hours of isoelectric focusing in a ZOOM® IPGRunner cassette (Invitrogen Corp., Carlsbad, Calif.), according to one embodiment of the present invention.

Following isoelectric focusing, electrode wick fibers were disentangled from the gel matrix under the acidic electrode to reveal visible, gel-embedded crystals that were also examined microscopically as shown in FIG. 4.

A portion of the gel was first cut to circumscribe one of the crystals, then scraped off the IPG strip backing, and finally scooped up by and onto a nylon fiber loop where the gel piece was dried at room temperature.

X-ray diffraction images were collected directly using the loop-and-gel-mounted crystal. The crystals appeared red in color to the naked eye during and after isoelectric focusing without the use of a microscope, which provides evidence of the expected presence of native, non-denatured, concentrated, ligand-containing protein.

All patents and publications cited in this specification are herein incorporated by reference as if each had specifically and individually been incorporated by reference herein. Although the foregoing invention has been described in some detail by way of illustration and example, it will be readily apparent to those of ordinary skill in the art, in light of the teachings herein, that certain changes and modifications may be made thereto without departing from the spirit or scope of the appended claims.

What is claimed is:

1. A method of crystallizing at least one protein, the method comprising:
    electrophoretically focusing at least a first protein species within a matrix comprising an immobilized continuous pH gradient wherein the matrix is adherent to at least one solid backing member,
    wherein said at least one solid backing member and the polymer matrix adhered thereto is fashioned in the shape of a strip,
    wherein said strip is a prior-cast, dehydrated, immobilized pH gradient (IPG) strip,
    the protein being present in amount sufficient to permit crystallization within said pH gradient and isolating crystals of said at least first protein species.

2. The method of claim 1, wherein electrophoretic focusing of said at least first protein species comprises:
    hydratingly lodging the prior-cast, dehydrated, IPG strip within an enclosing member that permits spaced electrical communication with said strip; and then
    using said spaced electrical communication to establish a voltage gradient in the polymer matrix of said strip sufficient to effect electrophoretic focusing of proteins therein.

3. The method of claim 2, further comprising the prior step of inserting said prior-cast IPG strip in its dehydrated state within said enclosing member.

4. The method of claim 2, wherein said step of hydratingly lodging comprises:
    contacting said enclosed dehydrated IPG strip with an aqueous solution for a time sufficient to lodge said separation medium within said enclosing member.

5. The method of claim 2, wherein said IPG strip isoelectric focusing is performed in a system comprising:
    means for enclosing a plurality of said strips, said enclosing means permitting spaced electrical communication separately with each of said enclosed strips through respective first and second entries; and means responsive to an external compressive force for effecting spaced electrical communication by a single anode and single cathode simultaneously with each of said enclosed strips, wherein said electrical communication means is capable of distributing an external compressive force to urge said anode and said cathode toward said enclosing means with greater pressure at said first and second entries than elsewhere on said enclosing means.

6. A method of crystallizing at least one protein, comprising electrophoretically transporting at least a first protein species within a polymer matrix that includes at least 2 regions of different pH, wherein the isoelectric point of the protein falls outside of the pH regions of the polymer matrix, and the protein being present in an amount sufficient to permit formation of protein crystals at a terminal region of the polymer matrix.

7. The method of claim 6, wherein the polymer matrix comprises a continuous pH gradient.

8. The method of claim 6, further comprising excising the terminal region of the polymer matrix that includes the protein crystals.

9. The method of claim 8, further comprising analyzing the protein crystals using x-ray diffraction.

\* \* \* \* \*